US008999316B2

(12) United States Patent
Engel et al.

(10) Patent No.: US 8,999,316 B2
(45) Date of Patent: Apr. 7, 2015

(54) ANTIVIRAL COMPOUNDS

(75) Inventors: Robert Engel, Carle Place, NY (US); JaimeLee Iolani Rizzo, Glen Cove, NY (US); Karin Melkonian Fincher, Garden City, NY (US)

(73) Assignees: Pace University, New York, NY (US); The Research Foundation Of The City Of New York, New York, NY (US); Long Island University, Brookville, NY (US)

( * ) Notice: Subject to any disclaimer, the term of this patent is extended or adjusted under 35 U.S.C. 154(b) by 1352 days.

(21) Appl. No.: 12/130,303

(22) Filed: May 30, 2008

(65) Prior Publication Data

US 2008/0299070 A1 Dec. 4, 2008

Related U.S. Application Data

(60) Provisional application No. 60/940,839, filed on May 30, 2007, provisional application No. 60/942,037, filed on Jun. 5, 2007.

(51) Int. Cl.
| | | |
|---|---|---|
| A61K 31/785 | (2006.01) | |
| A61P 31/12 | (2006.01) | |
| A01N 43/90 | (2006.01) | |
| D06M 13/477 | (2006.01) | |
| D06M 16/00 | (2006.01) | |

(52) U.S. Cl.
CPC .............. *A61K 31/785* (2013.01); *A01N 43/90* (2013.01); *D06M 13/477* (2013.01); *D06M 16/00* (2013.01)

(58) Field of Classification Search
None
See application file for complete search history.

(56) References Cited

U.S. PATENT DOCUMENTS

| | | | |
|---|---|---|---|
| 5,263,992 A | 11/1993 | Guire | |
| 5,476,509 A | 12/1995 | Keogh et al. | |
| 5,531,984 A * | 7/1996 | Staats | 424/78.07 |
| 6,033,719 A | 3/2000 | Keogh | |
| 6,299,604 B1 | 10/2001 | Ragheb et al. | |
| 6,306,454 B1 | 10/2001 | Ung-Chhun et al. | |
| 6,436,419 B1 | 8/2002 | Sun et al. | |
| 6,444,415 B1 | 9/2002 | Tanaka et al. | |
| 7,285,286 B2 | 10/2007 | Engel et al. | |
| 2004/0116551 A1* | 6/2004 | Terry | 523/122 |
| 2005/0181006 A1 | 8/2005 | Engel et al. | |
| 2006/0041123 A1 | 2/2006 | Axten et al. | |
| 2006/0128850 A1 | 6/2006 | Jariwala et al. | |

FOREIGN PATENT DOCUMENTS

| | | |
|---|---|---|
| EP | 0514588 | 11/1997 |
| WO | WO00/15897 | 3/2000 |
| WO | WO 03/086477 | * 10/2003 |

OTHER PUBLICATIONS

Cohen et al., "Polycations. 15. Polyammonium Surfaces—A New Approach to Antifungal Activity", 2004, Letters in Drug Design & Discovery, 1: 88-90.*
Cohen et al., "Polycations. IX. Polyammonium derivatives of cyclodextrins: syntheses and binding to organic oxyanions;" Heteroatom Chemistry. 11:546-555, 2000.
Fabian et al., "Polycations: Syntheses of polyammonium strings as antibacterial agents;" SYNLETT. 1007-1009, Aug. 1997.
Strekas et al., "Polycations 5. Inducement of DNA circular dichroism signals for duplex deoxyribonucleotide homopolymers by polycationic strings;" Archives of Biochemistry and Biophysics. 364(1):129-131, 1999.
Kanazawa et al., "Polymeric phosphonium salts as a novel class of cationic biocides. III. Immobilization of phosphonium salts by surface photografting and antibacterial activity of the surface-treated polymer films;" Journal of Polymer Science. 31:1467-1472, 1993.
Tiller et al., "Designing surfaces that kill bacteria on contact;" PNAS. 98(11):5981-5985, May 22, 2001.
Isquith et al., "Surface-bonded antimicrobial activity of an organosilicon quaternary ammonium chloride;" Applied Microbiology. 24(6):859-863, Dec. 1972.
Krause, "A universal technique for antimicrobial surface preparation using quaternary ammonium-functionalized dendrimers;" http://es.eps.gov/ncer_abstracts/sbir/02/phase1/pollution/krause.html, Sep. 27, 2002.

* cited by examiner

*Primary Examiner* — Robert A Wax
*Assistant Examiner* — Randeep Singh
(74) *Attorney, Agent, or Firm* — Hoffman & Baron, LLP

(57) ABSTRACT

The present invention relates to novel antiviral compounds which are covalently attached to solid, macro surfaces. In another embodiment, the invention relates to novel antiviral compositions including a polymeric material and, embedded therein, an antiviral compound. In other embodiments, the invention relates to making a surface antiviral and making a polymeric material antiviral.

2 Claims, No Drawings

ANTIVIRAL COMPOUNDS

CROSS-REFERENCE TO RELATED APPLICATIONS

This application claims the benefit of U.S. Provisional Application Ser. Nos. 60/940,839 filed May 30, 2007 and 60/942,037 filed Jun. 5, 2007, which are incorporated herein by reference.

SUMMARY OF THE INVENTION

The present invention relates to an antiviral surface having the formula (I):

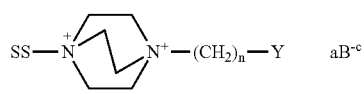
(I)

wherein:
SS represents a modified solid, macro surface comprising polymeric molecules having more than one primary hydroxyl group in the unmodified state;
n represents an integer from 2-8;
Y represents $-NR_2$, $-^+NR_3$, $-PR_2$, $-^+PR_3$, $-OH$, $-SH$, $-SR$, $-^+SR_2$, $-SO_3^-$, $-SO_2-OR$, $-OR$, $-C(O)R$, $-C(O)OR$, or a diazabicyclo[2.2.2]octane derivative selected from:

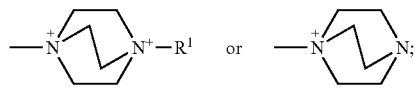

R independently represents H, $C_{1-4}$ alkyl, or phenyl;
$R^1$ represents H, $C_{1-4}$ alkyl, phenyl, $-NR_2$, $-PR_2$, $-^+PR_3$, $-OH$, $-SH$, $-SR$, $-^+SR_2$, $-SO_3^-$, $-OR$, $-C(O)R$, $-C(O)OR$, or $-SO_2-OR$;
B represents an anion;
a represents an integer;
c represents the valence of B, and is equal to 1-3;
wherein a×c represents a number such that the compound is charge balanced; and
with the proviso that the macro surface is not α-cyclodextrin or β-cyclodextrin.
In a preferred embodiment, Y represents

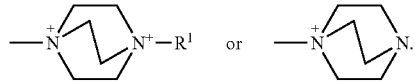

The invention also relates to an antiviral surface having the formula (III):

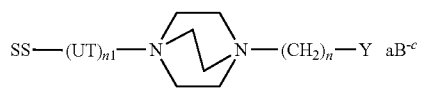
(III)

wherein:
SS represents a modified solid, macro surface comprising polymeric molecules having more than one primary hydroxyl group in the unmodified state;
U represents $-O-$, $-S-$, $-NQ-$ or $-SiR^2{}_2-$;
Q represents H, a hydrocarbon group comprising a minimum of 1 carbon atom and a maximum of 24 carbon atoms, phenyl, or benzyl;
$R^2$ represents a hydrocarbon group comprising a minimum of 1 carbon atom and a maximum of 24 carbon atoms, phenyl, or benzyl;
T represents a hydrocarbon chain comprising a minimum of 1 carbon atom and a maximum of 24 carbon atoms;
n1 represents 0 or 1;
n represents an integer from 2-8;
Y represents $-NR_2$, $-^+NR_3$, $-PR_2$, $-^+PR_3$, $-OH$, $-SH$, $-SR$, $-^+SR_2$, $-SO_3^-$, $-SO_2-OR$, $-OR$, $-C(O)R$, $-C(O)OR$, or a diazabicyclo[2.2.2]octane derivative selected from:

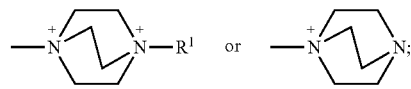

R independently represents H, $C_{1-4}$ alkyl, or phenyl;
$R^1$ represents H, $C_{1-4}$ alkyl, phenyl, $-NR_2$, $-PR_2$, $-^+PR_3$, $-OH$, $-SH$, $-SR$, $-^+SR_2$, $-SO_3^-$, $-OR$, $-C(O)R$, $-C(O)OR$, or $-SO_2-OR$;
B represents an anion;
a represents an integer;
c represents the valence of B, and is equal to 1-3;
wherein a×c represents a number such that the compound is charge balanced; and
with the proviso that the macro surface is not α-cyclodextrin or β-cyclodextrin.

The invention also relates to a solid antiviral composition comprising
a) a polymeric material that is solid at room temperature and molten at elevated temperatures and, embedded therein;
b) a compound of formula (II):

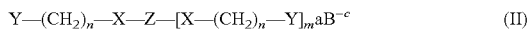
(II)

wherein:
Z represents a modified polyol having more than one primary hydroxyl group in the unmodified state, wherein at least two of the primary hydroxyl groups have been replaced by $X-(CH_2)_n-Y$ groups;
X represents

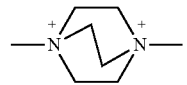

n independently represents an integer from 2-8;
Y represents $-NR_2$, $-^+NR_3$, $-PR_2$, $-^+PR_3$, $-OH$, $-SH$, $-SR$, $-^+SR_2$, $-SO_3^-$, $-SO_2-OR$, $-OR$, $-C(O)R$, $-C(O)OR$, or a diazabicyclo[2.2.2]octane derivative selected from:

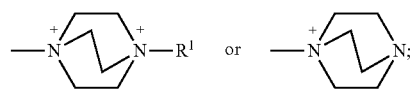

R independently represents H, $C_{1-4}$ alkyl, or phenyl;

$R^1$ represents H, $C_{1-4}$ alkyl, phenyl, $-NR_2$, $-PR_2$, $-^+PR_3$, $-OH$, $-SH$, $-SR$, $-^+SR_2$, $-SO_3^-$, $-OR$, $-C(O)R$, $-C(O)OR$, or $-SO_2-OR$;

m represents any number up to $m^1-1$ wherein $m^1$ represents the number of primary hydroxyl groups in the polyol in the unmodified state;

B represents an anion;

a represents an integer; and c represents the valence of B, and is equal to 1-3;

wherein a×c represents a number such that the compound is charge balanced.

Another aspect of the invention relates to a method for protecting a surface from viral contamination, the method comprising converting the surface to an antiviral surface having the formula (I):

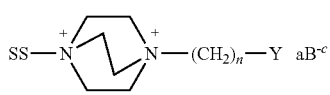

(I)

wherein:

SS represents a solid, macro surface comprising polymeric molecules having more than one primary hydroxyl group;

n represents an integer from 2-8;

Y represents $-NR_2$, $-^+NR_3$, $-PR_2$, $-^+PR_3$, $-OH$, $-SH$, $-SR$, $-^+SR_2$, $-SO_3^-$, $-SO_2-OR$, $-OR$, $-C(O)R$, $-C(O)OR$, or a diazabicyclo[2.2.2]octane derivative selected from:

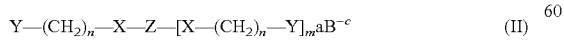

R independently represents H, $C_{1-4}$ alkyl, or phenyl;

$R^1$ represents H, $C_{1-4}$ alkyl, phenyl, $-NR_2$, $-PR_2$, $-PR_3$, $-OH$, $-SH$, $-SR$, $-^+SR_2$, $-SO_3^-$, $-OR$, $-C(O)R$, $-C(O)OR$, or $-SO_2-OR$;

B represents an anion;

a represents an integer;

c represents the valence of B, and is equal to 1-3;

wherein a×c represents a number such that the compound is charge balanced; and with the proviso that the macro surface is not α-cyclodextrin or β-cyclodextrin.

The invention also relates to a method for protecting a polymeric material from viral contamination, the method comprising converting the polymeric material to a solid antiviral composition comprising a) a polymeric material that is solid at room temperature and molten at elevated temperatures and, embedded therein;

b) a compound of formula (II):

$$Y-(CH_2)_n-X-Z-[X-(CH_2)_n-Y]_m aB^{-c} \quad (II)$$

wherein:

Z represents a modified polyol having more than one primary hydroxyl group in the unmodified state, wherein at least two of the primary hydroxyl groups have been replaced by $X-(CH_2)_n-Y$ groups;

X represents

n independently represents an integer from 2-8;

Y represents $-NR_2$, $-^+NR_3$, $-PR_2$, $-^+PR_3$, $-OH$, $-SH$, $-SR$, $-^+SR_2$, $-SO_3^-$, $-SO_2-OR$, $-OR$, $-C(O)R$, $-C(O)OR$, or a diazabicyclo[2.2.2]octane derivative selected from:

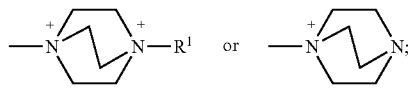

R independently represents H, $C_{1-4}$ alkyl, or phenyl;

$R^1$ represents H, $C_{1-4}$ alkyl, phenyl, $-NR_2$, $-PR_2$, $-^+PR_3$, $-OH$, $-SH$, $-SR$, $-^+SR_2$, $-SO_3^-$, $-OR$, $-C(O)R$, $-C(O)OR$, or $-SO_2-OR$;

m represents any number up to $m^1-1$ wherein $m^1$ represents the number of primary hydroxyl groups in the polyol in the unmodified state;

B represents an anion;

a represents an integer; and c represents the valence of B, and is equal to 1-3;

wherein a×c represents a number such that the compound is charge balanced.

DETAILED DESCRIPTION

Various surfaces and polymeric materials may be protected from viral contamination by converting the surfaces and polymeric materials to antiviral surfaces and polymeric materials in accordance with the invention. Antiviral compounds of the invention may be applied to various surfaces and polymeric materials by methods known in the art. The antiviral compounds may, for example, be covalently bonded to a surface, coated on the surface, e.g. as a modified polyol, or embedded in a polymeric material. Such surfaces and methods for applying the antiviral compounds to the surfaces are discussed below; are described in exhibits A, B, C, and D attached hereto; and are described in PCT/US03/10419, PCT/US06/040587, provisional U.S. patent application 60/863,147, and provisional U.S. patent application 60/941,822. The discussions of surfaces and methods for applying the antiviral compounds to the surfaces in PCT/US03/10419, PCT/US06/040587, provisional U.S. patent application 60/863,147, and provisional U.S. patent application 60/941,822 are incorporated herein by reference.

In one embodiment, the invention relates to novel antiviral surfaces covalently bonded to antiviral compounds having formula I:

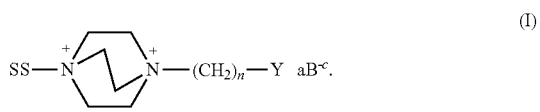

(I)

In formula I, SS represents a solid surface including polymeric molecules that has been modified by covalent attachment of the following moiety:

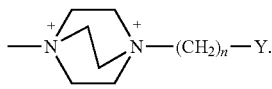

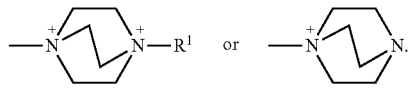

Preferably, the solid surface is a macro surface. A macro surface is a surface of an object that is significantly larger than a powder. Some examples of macro surfaces are fabrics or threads for making clothing or protective garments, plastic objects, medical devices, and wooden objects.

The solid surface can also be a micro surface. Micro surfaces include powders and nanoparticles. As defined in this specification, powders do not include α-cyclodextrin and β-cyclodextrin.

In its unmodified state, the solid surface comprises polymeric molecules having more than one primary hydroxyl group attached to a carbon or to a silicon atom. An unmodified surface can be a natural surface or a synthetic surface, and may, if necessary, be altered to comprise multiple hydroxyl groups. For example, polyesters can be altered in accordance with international PCT application US06/040587 to have primary hydroxyl groups.

An unmodified surface is made into a modified surface by converting the hydroxyl groups into electrophilic leaving groups, then treating the activated surface with an appropriate tertiary amine under conditions that cause the leaving group to be replaced by a nitrogen atom of the tertiary amine.

When the hydroxyl group is attached to a carbon atom in the unmodified solid surface, the surface will generally comprise natural polymers such as carbohydrates or proteins, or synthetic polymers, or mixtures thereof.

In this specification, carbohydrates refer to all polymers of (+)-glucose except α-cyclodextrin or β-cyclodextrin. Although carbohydrates include starch and glycogen, the carbohydrate of primary interest in the present specification is cellulose. The cellulose may, for example, be in the form of bulk cellulose, or in the form of cotton, linen, rayon, or cellulose acetate. The cotton may, for example, be cotton cloth, cotton gauze or bulk cotton. The carbohydrates may also be in the form of wood or paper.

Other types of material wherein a surface hydroxyl group is attached to a carbon atom include proteinacious materials. Materials comprising proteins include wool and silk.

Each of the materials described above may exist by itself, or as blends with one or more other materials. For example, any of the forms of cellulose described above may be blended with other forms of cellulose. Similarly, any of the forms of proteinacious materials described above may be blended with other forms of proteinacious materials. Moreover, any of the forms of cellulose described above may be blended with any of the forms of proteinacious materials described above. For example, wool and silk may be blended with cotton. Also, any of the materials and blends described above may be blended with other natural or synthetic materials, such as nylon and polyesters.

When the hydroxyl group is attached to a silicon atom on the solid surface, the material comprising the solid surface is typically silica, e.g. glass. The glass modified in accordance with the present invention may, for example, be a mirror or part of a medical instrument.

In formula I, n represents an integer from 2-8. For example, n can be 2, 3, 4, 5, 6, 7, or 8.

Y represents —$NR_2$, —$^+NR_3$, —$PR_2$, —$^+PR_3$, —OH, —SH, —SR, —$^+SR_2$, —$SO_3^-$, —$SO_2$—OR, —OR, —C(O)R, —C(O)OR, or a diazabicyclo[2.2.2]octane derivative selected from:

In a preferred embodiment, Y represents one of the diazabicyclo[2.2.2]octane derivatives shown above. In another preferred embodiment, Y represents —$NR_2$, —$^+NR_3$, or —OH.

R independently represents H, $C_{1-4}$ alkyl, or phenyl. $C_{1-4}$ alkyl represents hydrocarbon groups of 1, 2, 3, or 4 carbon atoms in length. A hydrocarbon group is bonded at one end to another chemical moiety, e.g. an atom. For example, if Y represents —$NR_2$ wherein one R represents H and the other R represents $C_2$ alkyl, then Y is —$NHC_2H_5$.

$R^1$ independently represents H, $C_{1-4}$ alkyl, phenyl, —$NR_2$, —$PR_2$, —$^+PR_3$, —OH, —SH, —SR, —$^+SR_2$, —$SO_3^-$, —OR, —C(O)R, —C(O)OR, or —$SO_2$—OR.

In a preferred embodiment, Y represents

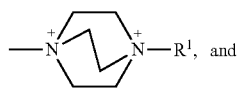

$R^1$ is $C_{1-4}$ alkyl.

The letters $aB^{-c}$ in formula I, and elsewhere in this application, represent the number and identity of anions necessary to maintain a charge-neutral compound. B represents any anion having a valence (c) of 1-3. Some examples of anions include monovalent anions such as halides (e.g., $F^-$, $Cl^-$, $Br^-$, and $I^-$), $OH^-$, and $H^-$ divalent anions such as $S^{-2}$, $CO_3^{-2}$, $SO_4^{-2}$, and trivalent anions such as $PO_4^{-3}$.

The letter a represents an integer such that the overall charge of the compound is neutral. For example, when the compound contains a divalent cation and B is $Cl^-$, then a is 2 and c is 1. In another example, when the compound contains a divalent cation and B is $S^{-2}$, then a is 1 and c is 2.

In another embodiment, the invention relates to novel antiviral surfaces having the formula III:

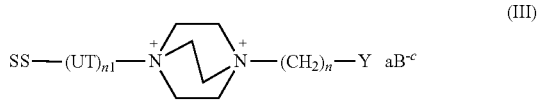

(III)

In formula III, the letters SS, n, Y, a, B, and c are as described above for formula I. n1 represents either 0 or 1. In this embodiment, the solid surface is preferably silica, e.g. glass.

The group UT in formula III is an optional linker. When UT is present (i.e. n1=1), U separates the solid surface (SS) and the positively charged nitrogen atom. When the group UT is absent (i.e. n1=0), the solid surface SS is bonded directly to the positively charged nitrogen atom.

For stability, the linking group UT is preferably present (i.e. n1=1) when the hydroxyl group on the unmodified solid surface is attached to a silicon atom, as, for example, in the case of silica, e.g. glass. Modified silica surfaces are more stable when the positively charged nitrogen atom in formula III is bonded to a carbon atom than when the positively charged nitrogen atom is bonded to a silicon atom. The carbon atom, e.g., a hydrocarbon chain, in turn, is covalently bonded to the oxygen atom of the hydroxyl group on the surface of the silica.

The letter III in formula III represents —O—, —S—, —NQ- or —SiR$^2{}_2$—. T represents a hydrocarbon chain comprising a minimum of 1 carbon atom and a maximum of 24 carbon atoms. Q represents H, a hydrocarbon group comprising a minimum of 1 carbon atom and a maximum of 24 carbon atoms, phenyl, or benzyl. Preferably, Q represents hydrogen, methyl, or ethyl. R$^2$ represents a hydrocarbon group comprising a minimum of 1 carbon atom and a maximum of 24 carbon atoms, phenyl, or benzyl.

In this specification, a distinction is made between hydrocarbon groups and hydrocarbon chains. A hydrocarbon group is bonded at only one end to another chemical moiety. A hydrocarbon chain is bonded independently at each end to another chemical moiety, e.g., to a group, or to an atom.

The carbon atoms of a group or chain can all be saturated, or can all be unsaturated. Alternatively, a chain can comprise a mixture of saturated and unsaturated carbon atoms. The unsaturated hydrocarbon chains contain one or more double and/or triple bonds.

In another embodiment, the invention relates to solid antiviral compositions consisting of a polymeric material and, embedded therein, an antiviral compound.

Any polymeric material that is solid at room temperature, and that is molten and stable at temperatures up to about 400° C. may be used in the invention. Preferably, the polymeric material is molten and stable at temperatures up to about 500° F. Examples of polymeric materials include, but are not limited to, polyvinyl chloride, polyester, polyethylene, polypropylene, polystyrene, polymethacrylate, polyacrylate, polyacrylaminde, nylon, and rayon. Other polymeric materials include natural and synthetic rubber.

An example of an antiviral compound that is embedded in a polymeric material or is coated on a surface is represented by formula II:

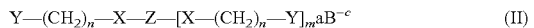

Z in formula II represents a modified polyol having more than one primary hydroxyl group in the unmodified state wherein at least two of the primary hydroxyl groups have been replaced by X—(CH$_2$)$_n$—Y groups. The unmodified polyol can be any molecule having more than one primary hydroxyl group. The unmodified polyol may, for example, be an alkane polyol, a polyether, a carbohydrate, or a protein.

An alkane polyol of the present invention is an alkane with a minimum of two carbon atoms and a maximum of twelve carbon atoms, and at least two primary hydroxyl groups. Some examples of alkane polyols include glycerol; mannitol; ethylene glycol; 1,5-pentanediol; 1,2,3,4,5,6,7,8-octaneoctol; 1,6,12-dodecanetriol; and 3-methanolyl-1,6-hexanehexyl.

The unmodified polyol can be a polyether. In this specification, polyether refers to molecules having at least two primary hydroxyl groups and having a minimum of one, and a maximum of about 10,000, preferably about 1,000, more preferably about 100, and most preferably about 10 ether groups. Some examples of polyethers include polyethylene glycol and polypropylene glycol.

Carbohydrates include saccharides, e.g., monosaccharides, oligosaccharides, and polysaccharides. The minimum number of saccharide units in an oligosaccharide is two. The maximum number of saccharide units in an oligosaccharide is twelve, preferably ten.

Polysaccharides have more than twelve saccharide units, and may have up to several thousand units, e.g. up to a maximum of about 10,000. In this specification, polysaccharides refer to polymers of (+)-glucose, and include cellulose, starch and glycogen. The saccharides can be in either the D or L configuration. Saccharide units can be either aldoses or ketoses.

The number of carbons in a saccharide unit can be from three carbons to about six carbons. An example of a three carbon sugar is glyceraldehyde. Examples of four carbon sugars include erythrose and threose. Examples of five carbon sugars include ribose, arabinose, xylose and lyxose. Examples of six carbon sugars include allose, altrose, glucose, mannose, gulose, idose, galactose and talose. All of these saccharides further include the corresponding 2'-deoxy derivatives.

The polyol can be a polyamino acid having at least two amino acids with primary hydroxyl groups. Polyamino acids include oligopeptides and proteins. An oligopeptide has two to twelve amino acid residues. Typically, proteins have more than twelve amino acid residues and up to about 1,000 amino acid residues.

The letter X in formula II represents 1,4-diazoniabicyclo[2.2.2.]octane, as shown below.

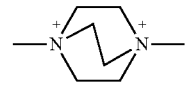

The letters n, Y, R, R$^1$, B, a, and c in formula II are as described above for formula I.

The letter m in formula II represents the number of hydroxyl groups that have been replaced by X—(CH$_2$)$_n$—Y, and may be any number greater than zero and up to m$^1$−1 wherein m$^1$ represents the number of primary hydroxyl groups in the unmodified polyol, Z. The minimum values for m$^1$ are two, four, and six. The maximum number for m$^1$ depends upon the type of polyol.

Carbohydrates can contain several thousand saccharide units. Each saccharide unit typically contains one primary hydroxyl group. Typically, for a carbohydrate, m$^1$ should not be greater than 10,000.

Proteins may contain up to 1,000 amino acid residues and sometimes more. A typical protein contains about 300 amino acid residues. Of the twenty naturally occurring amino acids, only serine contains a primary hydroxyl group. Typically, m$^1$ is not greater than 200 for a protein.

Preferably, alkane polyols of the present invention contain a minimum of two carbon atoms and a maximum of twelve carbon atoms, and at least two primary hydroxyl groups. Typically, m$^1$ is not greater than eight for an alkane polyol of the present invention.

An unmodified polyol is made into a modified polyol by converting the hydroxyl groups into electrophilic leaving groups, then treating the activated polyol with an appropriate tertiary amine under conditions that cause the leaving group to be replaced by a nitrogen atom of the tertiary amine.

It is not necessary to activate all of the available primary hydroxyl sites present on the surface of a material. For example, less than about 10% of the available hydroxyl groups on a surface may be activated to subsequently provide sufficient antiviral activity. Preferably, about 25% of the available hydroxyl groups may be activated, more preferably about 50%, and most preferably about 75% of the available hydroxyl groups may be activated.

For example, when Z is a carbohydrate comprising 2,000 glucose units, m$^1$ is 2,000, and m may be any number up to 1,999. An antiviral composition for a 2,000 unit carbohydrate may, for instance, have a value for m of 1,500.

In another example, when Z is a protein comprising 300 amino acid residues, fifteen of which are serine, $m^1$ is fifteen, and m may be any number up to fourteen. An antiviral composition for a 300 residue protein may, for instance, have a value for m of seven.

In yet another example, when Z is 2,3-hydroxymethyl-1,4-butanediol, the alkane polyol contains four primary hydroxyl groups. The value of $m^1$ is four and m may be any number up to three. An antiviral composition for 2,3-hydroxymethyl-1,4-butanediol may, for instance, have a value for m of two.

Modification of Surfaces

Activation of Hydroxyl Groups for Covalent Attachment of Tertiary Amines

Surfaces can be modified in accordance with the invention by methods known in the art. In the case of surfaces that have primary hydroxyl groups attached to carbon atoms, for example, carbohydrate and protein surfaces, activation of surface hydroxyl groups may be accomplished by converting the hydroxyl group to an active ester.

Hydroxyl groups may be converted to active esters by reacting the hydroxyl groups with an esterification reagent in a suitable medium. Suitable reagents include, for example, benzenesulfonyl chloride, p-toluenesulfonyl chloride, thionyl chloride, and phosphorus tribromide. Suitable media for the reaction include, but are not limited to, pyridine, hexane, heptane, ether, toluene, ethyl acetate, and mixtures thereof. The amount of reagent and volume of suitable medium are known to those in the art.

Equation 1 below depicts an example of the activation of hydroxyl groups on one of multiple units of a carbohydrate by reaction with p-toluenesulfonyl chloride:

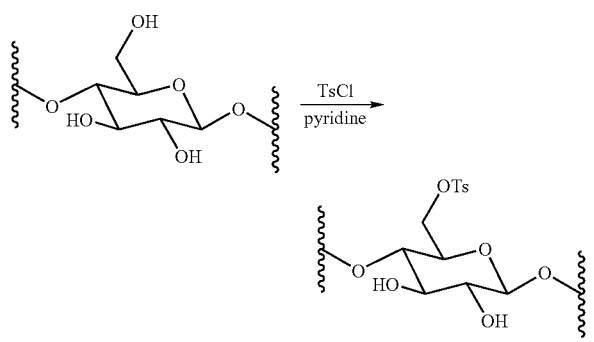

Equation 1

The activation reaction requires a proton-sink. When pyridine is used as the medium, pyridine functions as its own proton-sink. The use of pyridine may be avoided, for example, by using one of the other, inert solvent systems disclosed above, and adding an alkaline compound, such as an insoluble polymeric tertiary amine, to act as the proton-sink. The insoluble polymeric tertiary amine, may be, for example, DEAE-cellulose.

Hydroxyl groups attached to silicon atoms can be modified in the same way as chromatographic media, as is known in the art. For example, such hydroxyl groups may be treated with various substituted halosilanes, such as chlorosilanes or bromosilanes, in a non-reactive (i.e., non-hydroxylic, non-acidic) solvent. The halosilane may have the following structure:

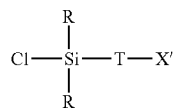

where X' is Cl, Br, or I, and T and R are as described above.

Treatment of the hydroxyl group with, for example, chlorosilane results in binding of the Si atom to the oxygen of the surface hydroxyl group, thus liberating HCl. This reaction provides a linker which can be used for the attachment of a positively charged moiety.

Equation 2 below depicts an example of the activation of hydroxyl groups on silica with a chlorosilane:

Equation 2

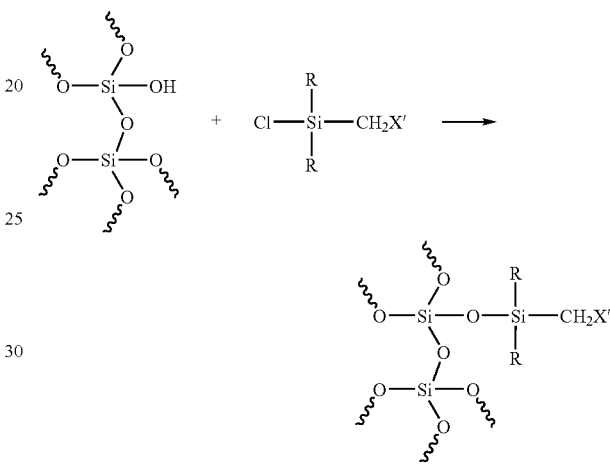

Examples of non-reactive solvents for use in activation of hydroxyl groups on silica surfaces, include, but are not limited to, solvents such as ether, a hydrocarbon, an ester, e.g. ethyl acetate and a simple nitrile, e.g. acetonitrile.

Covalent Attachment of Tertiary Amine Group

The surfaces (e.g., carbohydrate, protein, and silica) activated by the process described above are rendered antiviral by the chemical attachment of a suitable tertiary amine in a suitable reaction medium. Some examples of suitable reaction media include, acetonitrile, ethanol, methanol, 2-propanol, propionitrile, and mixtures thereof.

An example of the attachment of a positively charged moiety, 4-hexyl-1-aza-4-azoniabicyclo[2.2.2]octane to an active group on one of multiple units of a carbohydrate is shown in equation 3 below:

Equation 3

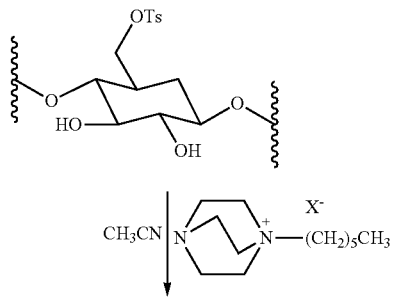

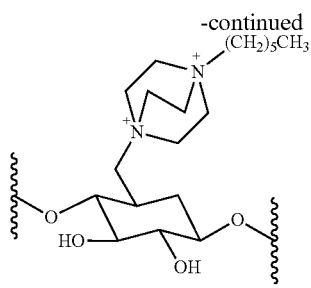

The synthesis of polyammonium species is known in the art. For example, see Fabian, et al. "Polycations: Syntheses of Polyammonium Strings as Antibacterial Agents," Synlett, August 1997.

An example of the attachment of a positively charged moiety, 1-aza-4-(hexyl)azonia-[2,2,2]-bicyclooctane to an active group on silica is shown in equation 4 below, wherein R, X, and X' are as described above:

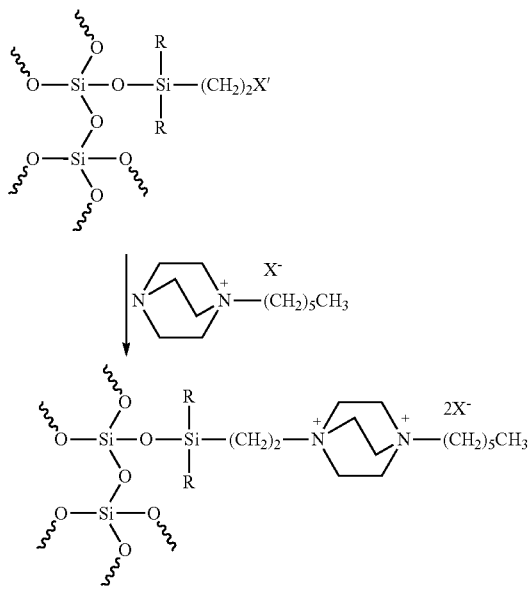

Equation 4

Once the modification of a antiviral surface is complete, the prepared surface may be sequentially washed with a solvent used for the final reaction (e.g., reaction medium used in attachment of positively charged moiety), brine and water, and then dried.

Method of Embedding

The embedded polymeric materials can be made by methods known in the art. For example, embedding is discussed in U.S. patent application Ser. No. 12/129,805, the section of which entitled "Method of Embedding" is incorporated herein by reference.

In one embodiment, the invention is related to a method of making an antiviral composition by providing a polymeric material, such as those described above, that is in a solid state at room temperature; melting the polymeric material at temperatures up to about 400° C. to form a molten polymeric material; adding an antiviral compound described above to the molten polymeric material to form a mixture of the compound embedded in the polymeric material; and cooling the mixture until it solidifies. Preferably, the polymeric material is heated up to temperatures of about 500° F. The antiviral compound may be added to the molten polymeric material by any suitable method. For example, the antiviral compound may be applied to the surface of the polymeric material before or after melting the polymeric material, or by injecting the antiviral compound into the molten polymeric material. All other steps are as described above.

The polymeric material may be heated by any known method. Preferred methods include convection heating, microwave heating, and contact heating.

The polymeric material and embedded compound are as described above. A polymeric material is molten when it is sufficiently fluid that a chemical compound can be dispersed within it.

The compound may be evenly dispersed within the polymeric material. Alternatively, the compound may be concentrated within the area surrounding the surface of the polymeric material.

For example, the heating of the solid polymeric material may be controlled, e.g. in an oven, so that only up to 5%, 10%, 25%, or 50% of the outer portion of the material becomes molten. Then the antiviral compound is added to the molten material. Once, the polymeric material is cooled and solidifies, the area surrounding the surface of the material will be antiviral.

The antiviral compound may be applied to the polymeric material before or after it is made molten by any method known in the art. For example, the antiviral compound may be in a solution that is applied to the polymeric material. The solution may be applied to the polymeric material by known methods such as coating, spraying, paddling, application by laundry equipment, exhausting on dyeing machinery, or dipping.

Antiviral Compositions

The polymeric materials of the invention may be used to make numerous products that may benefit from antiviral activity. For example, antiviral compounds of the invention are advantageously embedded in or applied to working surfaces in vehicles, public and private facilities, places of commerce, homes, factories, offices and establishments, including walls, floors, furniture, as well as HVAC, plumbing and other equipment; in textiles and fabrics, building products, cellulose and paper goods; and also in medical articles and personal articles, including but not limited to those for protection and treatment, for personal care, and for various articles of wear, and for other uses. Additional examples of products made from polymeric material in which antiviral compounds may be embedded in or applied to include, but are not limited to, furniture, Petri dishes, clothing, countertops, condoms, tents, shower curtains, brushes, toys, flooring covers, gymnastic equipment (including mats), hot tubs, food and beverage containers, plastic bags, cutting boards, toilet seats, animal carriers, litter boxes, door mats, pool liners, adhesive bandages, telephones, keyboards, shoes, and insoles. Further examples of products made from the polymeric materials of the invention include plastic syringes, plastic tubing, and any other plastic devices used in hospitals. Some additional examples of products include, but are not limited to, paints, cosmetics (e.g., lipsticks, chapped lip treatments, ointments and creams, mascaras, etc.) brushes, clothing, dressing and bandages.

Antiviral Activity

The embedded polymeric materials according to the invention demonstrate antiviral properties against any virus. In this specification, antiviral properties refer to the ability to reduce the number of viral particles on a surface.

Some examples of viruses susceptible to the compounds of the present invention include: Abelson leukemia virus, Abelson murine leukemia virus, Abelson's virus, acute laryngotracheobronchitis virus, Adelaide River virus, adeno associated virus group, Adenovirus, African horse sickness virus, African swine fever virus, AIDS virus, Aleutian mink disease parvovirus, alfalfa mosaic virus, alpharetrovirus, Alphavirus, ALV related virus, Amapari virus, Andean potato mottle virus, Aphthovirus, Aquareovirus, arbovirus, arbovirus C, arbovirus group A, arbovirus group B, Arenavirus group, Argentine hemorrhagic fever virus, Argentinian hemorrhagic fever virus, Arterivirus, Astrovirus, Ateline herpesvirus group, Aujezky's disease virus, Aura virus, Ausduk disease virus, Australian bat lyssavirus, Aviadenovirus, avian erythroblastosis virus, avian infectious bronchitis virus, avian leukemia virus, avian leukosis virus, avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus, B19 virus, Babanki virus, baboon herpesvirus, bacterial virus, baculovirus, barley yellow dwarf virus, Barmah Forest virus, bean pod mottle virus, bean rugose mosaic virus, Bebaru virus, Berrimah virus, betaretrovirus, Birnavirus, Bittner virus, BK virus, Black Creek Canal virus, bluetongue virus, Bolivian hemorrhagic fever virus, Boma disease virus, border disease of sheep virus, borna virus, bovine alphaherpesvirus 1, bovine alphaherpesvirus 2, bovine coronavirus, bovine ephemeral fever virus, bovine immunodeficiency virus, bovine leukemia virus, bovine leukosis virus, bovine mammillitis virus, bovine papillomavirus, bovine papular stomatitis virus, bovine parvovirus, bovine syncytial virus, bovine type Concovirus, bovine viral diarrhea virus, bracovirus, broad bean mottle virus, broad bean stain virus, brome mosaic virus, Bromovirus, Buggy Creek virus, bullet shaped virus group, Bunyamwera virus supergroup, Bunyavirus, Burkitt's lymphoma virus, Bwamba Fever—Bwattany hetero virus, CA virus, Calicivirus, California encephalitis virus, camelpox virus, canarypox virus, canid herpesvirus, canine coronavirus, canine distemper virus, canine herpesvirus, canine minute virus, canine parvovirus, Cano Delgadito virus, Capillovirus, caprine arthritis virus, caprine encephalitis virus, Caprine Herpes Virus—Capripox virus, Cardiovirus, Carlavirus, Carmovirus, carrot mottle virus, Cassia yellow blotch virus, Caulimovirus, Cauliflower mosaic virus—caviid herpesvirus 1, Cercopithecine herpesvirus 1, Cercopithecine herpesvirus 2, cereal yellow dwarf virus, Chandipura virus, Changuinola virus, channel catfish virus, Charleville virus, chickenpox virus, Chikungunya virus, chimpanzee herpesvirus, chub reovirus, chum salmon virus, Closterovirus, Cocal virus, Coho salmon reovirus, coital exanthema virus, Colorado tick fever virus, Coltivirus, Columbia SK virus, Commelina yellow mottle virus, common cold virus, Comovirus, congenital cytomegalovirus, contagious eethyma virus, contagious pustular dermatitis virus, Coronavirus, Corriparta virus, coryza virus, cowpea chlorotic mottle virus, cowpea mosaic virus, cowpea virus, cowpox virus, coxsackie virus, CPV (cytoplasmic polyhedrosis virus), cricket paralysis virus, Crimean-Congo hemorrhagic fever virus, croup associated virus, Crypotovirus, Cucumovirus, Cypovirus, cytomegalovirus, cytomegalovirus group, cytoplasmic polyhedrosis virus, deer papillomavirus, defective virus, deltaretrovirus, dengue virus, Densovirus, Dependovirus, Dhori virus, Dianthovirus, diploma virus, DNA virus, Drosophila C virus, duck hepatitis B virus, duck hepatitis virus 1, duck hepatitis virus 2, duovirus, Duvenhage virus, Deformed wing virus DWV, eastern equine encephalitis virus, eastern equine encephalomyelitis virus, EB virus, Ebola virus, Ebola-like virus, echo virus, echovirus, echovirus 10, echovirus 28, echovirus 9, ectromelia virus, EEE virus, EIA virus, EMC virus, Emiliania huxleyi virus 86, encephalitis virus, encephalomyocarditis group virus, encephalomyocarditis virus, Enterovirus, enzyme elevating virus, enzyme elevating virus (LDH), epidemic hemorrhagic fever virus, epizootic hemorrhagic disease virus, Epstein-Barr virus, equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillomavirus, European swine fever virus, Everglades virus, Eyach virus, Fabavirus, felid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus, feline syncytial virus, Fijivirus, Filovirus, Flanders virus, Flavivirus, foot and mouth disease virus, Fort Morgan virus, Four Corners hantavirus, fowl adenovirus 1, fowlpox virus, Friend virus, Furovirus, gammaretrovirus, GB hepatitis virus, GB virus, Geminivirus, German measles virus, Getah virus, gibbon ape leukemia virus, glandular fever virus, goatpox virus, golden shinner virus, Gonometa virus, goose parvovirus, granulosis virus, Gross' virus, ground squirrel hepatitis B virus, group A arbovirus, Guanarito virus, guinea pig cytomegalovirus, guinea pig type C virus, Gay elephant tycomabanucleoid virus, Hantaan virus, Hantavirus, hard clam reovirus, hare fibroma virus, HCMV (human cytomegalovirus), helper virus, hemadsorption virus 2, hemagglutinating virus of Japan, hemorrhagic fever virus, hendra virus, Henipaviruses, Hepadnavirus, hepatitis A virus, hepatitis B virus group, hepatitis C virus, hepatitis D virus, hepatitis delta virus, hepatitis E virus, hepatitis F virus, hepatitis G virus, hepatitis nonA nonB virus, hepatitis virus, hepatitis virus (nonhuman), hepatoencephalomyelitis reovirus 3, Hepatovirus, heron hepatitis B virus, herpes B virus, herpes simplex virus, herpes simplex virus 1, herpes simplex virus 2, herpesvirus, herpesvirus 7, Herpesvirus ateles, Herpesvirus hominis, Herpesvirus infection, Herpesvirus saimiri, Herpesvirus suis, Herpesvirus varicellae, Highlands J virus, Hirame rhabdovirus, hog cholera virus, Hordeivirus, human adenovirus 2, human alphaherpesvirus 1, human alphaherpesvirus 2, human alphaherpesvirus 3, human B lymphotropic virus, human betaherpesvirus 5, human coronavirus, human cytomegalovirus group, human foamy virus, human gammaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immunodeficiency virus, human immunodeficiency virus 1, human immunodeficiency virus 2, human papillomavirus, human T cell leukemia virus, human T cell leukemia virus I, human T cell leukemia virus II, human T cell leukemia virus III, human T cell lymphoma virus I, human T cell lymphoma virus II, human T cell lymphotropic virus type 1, human T cell lymphotropic virus type 2, human T lymphotropic virus I, human T lymphotropic virus II, human T lymphotropic virus III, ichnovirus, Ilarvirus, infantile gastroenteritis virus, infectious bovine rhinotracheitis virus, infectious haematopoietic necrosis virus, infectious pancreatic necrosis virus, influenza A virus, influenza B virus, influenza virus (unspecified), influenzavirus (unspecified), influenzavirus A, influenzavirus B, influenzavirus C, influenzavirus D, influenzavirus pr8, insect iridescent virus, insect virus, interfering virus, iridovirus, Japanese B virus, Japanese encephalitis virus, JC virus, Junin virus, Kaposi's sarcoma-associated herpesvirus, Kemerovo virus, Kilham's rat virus, Klamath virus, Kolongo virus, Korean hemorrhagic fever virus, kumba virus, Kysanur forest disease virus, Kyzylagach virus, La Crosse virus, lactic dehydrogenase elevating virus, lactic dehydrogenase virus, Lagos bat virus, Lambda phage, Langur virus, lapine parvovirus, Lassa fever virus, Lassa virus, latent rat virus, LCM virus, Leaky virus, Lentivirus, Leporipoxvirus, leukemia virus, leukovirus, lumpy skin disease virus, Luteovirus, lymphadenopathy associated virus, Lymphocryptovirus, lymphocytic choriomeningitis virus, lymphoproliferative virus group, Lyssavirus, Machupo virus, mad itch virus, maize chlorotic dwarf virus, maize rough dwarf virus, mammalian type B oncovirus group, mammalian type B retroviruses, mammalian type C retrovirus group, mammalian type D retroviruses, mammary tumor virus, Mapuera virus, Marafivirus, Marburg virus, Marburg-like virus, Mason Pfizer monkey virus, Mastadenovirus, Mayaro virus, ME virus, measles virus, Melandrium yellow fleck virus—Menangle virus, Mengo virus, Mengovirus, Middelburg virus, milkers nodule virus, mink enteritis virus, minute virus of mice, MLV related virus, MM virus, Mokola virus, Molluscipoxvirus, Molluscum contagiosum virus, monkey B virus, monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyomavirus, mouse sarcoma virus, mousepox virus, Mozambique virus, Mucambo virus, mucosal disease virus, mumps virus, murid betaherpesvirus 1, murid cytomegalovirus 2, murine cytomegalovirus group, murine encephalomyelitis virus, murine hepatitis virus, murine leukemia virus, murine nodule inducing virus, murine polyomavirus, murine sarcoma virus, Muromegalovirus, Murray Valley encephalitis virus, myxoma virus, Myxovirus, Myxovirus multiforme, Myxovirus parotitidis, Nairobi sheep disease virus, Nairovirus, Nanirnavirus, Nariva virus, Ndumo virus, Necrovirus, Neethling virus, Nelson Bay virus, Neopvirus, neurotropic virus, New World Arenavirus, newborn pneumonitis virus, Newcastle disease virus, Nipah virus, noncytopathogenic virus, Noravirus, Norwalk virus, nuclear polyhedrosis virus (NPV)- nipple neck virus, O'nyong'nyong virus, oat sterile dwarf virus, Ockelbo virus, oncogenic virus, oncogenic viruslike particle, oncornavirus, Orbivirus, Orf virus, Oropouche virus, Orthohepadnavirus, orthomyxovirus, Orthopoxvirus, Orthoreovirus, Orungo, ovine papillomavirus, ovine catarrhal fever virus, owl monkey herpesvirus, Palyam virus, Papillomavirus, Papillomavirus sylvilagi, Papovavirus, parainfluenza virus, parainfluenza virus type 1, parainfluenza virus type 2, parainfluenza virus type 3, parainfluenza virus type 4, Paramyxovirus, Parapoxvirus, paravaccinia virus, parsnip yellow fleck virus, Parvovirus, Parvovirus B19, parvovirus group, pea enation mosaic virus, Pestivirus, Phlebovirus, phocine distemper virus, Phytoreovirus, Picodnavirus, Picornavirus, pig cytomegalovirus, pigeonpox virus, Piry virus, Pixuna virus, plant rhabdovirus group, plant virus, pneumonia virus of mice, Pneumovirus, poliomyelitis virus, poliovirus, Polydnavirus, polyhedral virus, polyoma virus, Polyomavirus, Polyomavirus bovis, Polyomavirus cercopitheci, Polyomavirus hominis 2, Polyomavirus maccacae 1, Polyomavirus muris 1, Polyomavirus muris 2, Polyomavirus papionis 1, Polyomavirus papionis 2, Polyomavirus sylvilagi, Pongine herpesvirus 1, porcine epidemic diarrhea virus, porcine hemagglutinating encephalomyelitis virus, porcine parvovirus, porcine transmissible gastroenteritis virus, porcine type C virus, Potato leaf roll virus, Potato mop top virus, Potato virus Y, Potexvirus, Potyvirus, pox virus, poxvirus, poxvirus variolae, Prospect Hill virus, provirus, pseudocowpox virus, pseudorabies virus, psittacinepox virus, Puumala virus, quailpox virus, rabbit fibroma virus, rabbit kidney vaculolating virus, rabbit papillomavirus, rabies virus, raccoon parvovirus, raccoonpox virus, radish mosaic virus, Ranikhet virus, rat cytomegalovirus, rat parvovirus, rat virus, Rauscher's virus, recombinant vaccinia virus, recombinant virus, reovirus, reovirus 1, reovirus 2, reovirus 3, reptilian type C virus, respiratory infection virus, respiratory syncytial virus, respiratory virus, reticuloendotheliosis virus, Retrovirus, Rhabdovirus, Rhabdovirus carpia, Rhadinovirus, rhinovirus, Rhizidiovirus, rice dwarf virus, rice gall dwarf virus, rice ragged stunt virus, Rift Valley fever virus, Riley's virus, rinderpest virus, RNA tumor virus, RNA virus, Ross River virus, Rotavirus, rougeole virus, Rous sarcoma virus, rubella virus, rubeola virus, Rubivirus, Russian autumn encephalitis virus, SA 11 simian virus, SA2 virus, Sabia virus, Sagiyama virus, Saimirine herpesvirus 1, salivary gland virus, sandfly fever virus group, Sandjimba virus, SARS virus, satellite virus, SDAV (sialodacryoadenitis virus), sealpox virus, Semliki Forest Virus, Sendai virus, Seoul virus, sheeppox virus, Shope fibroma virus, Shope papilloma virus, simian foamy virus, simian hepatitis A virus, simian human immunodeficiency virus, simian immunodeficiency virus, simian parainfluenza virus, simian T cell lymphotrophic virus, simian virus, simian virus 40, Simplexvirus, Sin Nombre virus, Sindbis virus, smallpox virus, Sobemovirus, South American hemorrhagic fever viruses, sparrowpox virus, spring beauty latent virus, Spumavirus, squash mosaic virus, squirrel fibroma virus, squirrel monkey retrovirus, SSV 1 virus group, STLV (simian T lymphotropic virus) type I, STLV (simian T lymphotropic virus) type II, STLV (simian T lymphotropic virus) type III, stomatitis papulosa virus, submaxillary virus, suid alphaherpesvirus 1, suid herpesvirus 2, Suipoxvirus, swamp fever virus, swinepox virus, Swiss mouse leukemia virus, T4 phage, T7 phage, TAC virus, Tacaribe complex virus, Tacaribe virus, Tanapox virus, Taterapox virus, Tench reovirus, Tenvivirus, Theiler's encephalomyelitis virus, Theiler's virus, Thogoto virus, Thottapalayam virus, Tick borne encephalitis virus, Tioman virus, tobacco mosaic virus, tobacco rattle virus, Tobamovirus, Tobravirus, Togavirus, tomato bushy stunt virus, Tomato spotted wilt virus, Tombusvirus, Torovirus, Tospovirus, transforming virus, tumor virus, Tupaia virus, turkey rhinotracheitis virus, turkeypox virus, turnip yellow mosaic virus, Tymovirus, type C retroviruses, type D oncovirus, type D retrovirus group, ulcerative disease rhabdovirus, Una virus, Uukuniemi virus group, vaccinia virus, vacuolating virus, varicella zoster virus, Varicellovirus, Varicola virus, variola major virus, variola virus, Vasin Gishu disease virus, VEE virus, Venezuelan equine encephalitis virus, Venezuelan equine encephalomyelitis virus, Venezuelan hemorrhagic fever virus, vesicular stomatitis virus, Vesiculovirus, Vilyuisk virus, viper retrovirus, viral haemorrhagic septicemia virus, Template:VIRUS76 viruslike particle, Visna Maedi virus, Visna virus, volepox virus, VSV (vesicular stomatitis virus), Wallal virus, Warrego virus, wart virus, WEE virus, West Nile virus, western equine encephalitis virus, western equine encephalomyelitis virus, Whataroa virus, Winter Vomiting Virus, woodchuck hepatitis B virus, woolly monkey sarcoma virus, wound tumor virus, WRSV virus, Yaba monkey tumor virus, Yaba virus, Yatapoxvirus, yellow fever virus, Yug Bogdanovac virus, and ZYMV (zucchini yellow mosaic virus).

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any two, three, or four of the members, e.g., a and c; a, d, and e; b, c, d, and e; etc.

In some cases, the members of a first group of parameters, e.g., a, b, c, d, and e, may be combined with the members of a second group of parameters, e.g., A, B, C, D, and E. Any member of the first group or of a sub-group thereof may be combined with any member of the second group or of a sub-group thereof to form additional groups, i.e., b with C; a and c with B, D, and E, etc.

For example, in the present invention, groups of various parameters are defined (e.g. R, $R^1$, SS, n, Y, B, a, and c). Each group contains multiple members. For example, R independently represents H, $C_{1-4}$ alkyl, or phenyl. Each member may be combined with each other member to form additional sub-groups, e.g., H and phenyl, H and $C_2$ alkyl, and $C_3$ alkyl and phenyl.

The instant invention further contemplates embodiments in which each element listed under one group may be combined with each and every element listed under any other group. For example, U is defined above as representing —O—, —S—, —NQ- or —$SiR^2{}_2$—. T is defined as representing a hydrocarbon chain comprising a minimum of 1 carbon atom and a maximum of 24 carbon atoms. Each element of U (—O—, —S—, —NQ- or —$SiR^2{}_2$—) can be combined with each and every element of T (a hydrocarbon chain comprising a minimum of 1 carbon atom and a maximum of 24 carbon atoms). For example, in one embodiment, U may be —O— and T may be a 14 carbon chain. Alternatively, U may be —S— and T may be a 6 carbon chain, etc. Similarly, a third group is n, in which the elements are defined as an integer from 2-8. Each of the above embodiments may be combined with each and every element of n. For example, in the embodiment wherein U is —O— and T is a 14 carbon chain, n may be 8 (or any other number within the element of n).

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

A list following the word "comprising" is inclusive or open-ended, i.e., the list may or may not include additional unrecited elements. A list following the words "consisting of" is exclusive or closed ended, i.e., the list excludes any element not specified in the list.

All numbers in the specification are approximate unless indicated otherwise.

The method of treating a condition, disorder or disease with a chemical compound or a chemical composition includes the use of the chemical compound or chemical composition in the manufacture of a medicament for the treatment of the condition, disorder or disease. A compound or a group of compounds said to be effective in treating a condition, disorder or disease includes the compound or group of compounds for use in treating the condition, disorder or disease.

EXAMPLES

Example 1

Preparation of
N-hexyl-N,N-dimethyl-N-(2-thiomethyl)ethylammonium bromide

The ammonium salt N-hexyl-N,N-dimethyl-N-(2-thiomethyl)ethylammoniumbromide is prepared by adding 66.1 g (0.210 mol) of 1-bromohexane in 150 ml of ethyl acetate to 25 g (0.210 mol) of N,N-dimethyl-N-(2-thiomethyl)ethylamine in 250 ml of ethyl acetate. The solution mixture is stirred. The resultant precipitate is collected by suction filtration and washed with ether and dried under vacuum.

Example 2

Preparation of Antiviral Cotton Cloth with
N-hexyl-N,N-dimethyl-N-(2-thiomethyl)ethylammonium bromide A 25 g sample of 100% cotton cloth is placed in a solution of 29.5 g of the activating agent p-toluenesulfonyl chloride (0.155 mol) in 150 ml pyridine as dispersing medium. The reaction medium is agitated overnight. The modified cotton cloth is removed and washed with ice-water. The washed modified cotton cloth is then placed with N-hexyl-N,N-dimethyl-N-(2-thiomethyl)ethylammonium bromide (62.4 g, 0.155 mol) in acetonitrile and is agitated overnight. The modified cotton cloth is then removed from the reaction mixture, washed sequentially with acetonitrile, brine and water, and dried in air.

Example 3

Preparation of Antiviral Cotton Cloth with
4-hexyl-1-aza-4-azoniabicyclo[2.2.2]octane chloride.

A 25 g sample of 100% cotton cloth (bearing a maximum of 0.465 equivalents of hydroxyl groups, approximately 0.155 equivalents of which are primary hydroxyl groups) is placed in a solution of 29.5 g of the activating agent p-toluenesulfonyl chloride (0.155 mol) in 150 ml pyridine as dispersing medium. The reaction medium is agitated overnight. The modified cotton cloth is removed and washed with ice-water. The washed modified cotton cloth is then placed in acetonitrile containing 57.74 g (0.155 mol) of 4-hexyl-1-aza-4-azoniabicyclo[2.2.2]octane chloride and the reaction mixture is agitated overnight. The modified cotton cloth is then removed from the reaction medium, washed sequentially with acetonitrile, brine and water, and dried in air.

Example 4

Preparation of Antiviral Wood

A 25 g sample of wood (maple) (bearing a maximum of 0.465 equivalents of hydroxyl groups, approximately 0.155 equivalents of which are primary hydroxyl groups) is placed in a solution of 29.5 g of the activating agent p-toluenesulfonyl chloride (0.155 mol) in 150 ml pyridine as dispersing medium. The reaction medium is agitated overnight. The modified wood is removed and washed with ice-water. The washed modified wood is then placed in acetonitrile containing 53.40 g (0.155 mol) of 4-hexyl-1-aza-4-azoniabicyclo[2.2.2]octane chloride and the reaction mixture was agitated overnight. The modified wood is then removed from the reaction medium, washed sequentially with acetonitrile, brine and water and dried in air.

Example 5

Preparation of Antiviral Silk

A 25 g sample of 100% silk (bearing a maximum of 0.057 equivalents of primary hydroxyl groups) is placed in a solution of 10.8 g of the activating agent p-toluenesulfonyl chloride (0.155 mol) in 150 ml pyridine as dispersing medium. The reaction medium is agitated overnight. The modified silk is removed and washed with ice-water. The washed modified silk is then placed in a solution of 21.2 g of 4-hexyl-1-aza-4-azoniabicyclo[2.2.2]octane chloride in 100 ml of acetonitrile and the reaction mixture is agitated overnight. The modified silk is then removed from the reaction medium, washed sequentially with acetonitrile, brine and water and dried in air.

Example 6

Preparation of Antiviral Wool with
4-hexyl-1-aza-4-azoniabicyclo[2.2.2]octane chloride A 25 g sample of 100% wool (bearing a maximum of 0.052 equivalents of hydroxyl groups) is placed in a solution of 9.90 g of the activating agent p-toluenesulfonyl chloride (0.155 mol) in 150 ml pyridine as dispersing medium. The reaction medium is agitated overnight. The modified wool is removed and washed with ice-water. The washed modified wool is then placed in a solution of 20.82 g (0.052 mol) of 4-hexyl-1-aza-4-azoniabicyclo[2.2.2]octane chloride in 100 ml of acetonitrile and the reaction mixture is agitated overnight. The modified wool is then removed from the reaction medium, washed sequentially with acetonitrile, brine and water and dried in air.

Example 7

Preparation of Antiviral Wool with
P-Hexyl-P,P-Diphenylphosphine

A 25 g sample of 100% wool (bearing a maximum of 0.052 equivalents of hydroxyl groups) is placed in a solution of 9.90 g of the activating agent p-toluenesulfonyl chloride (0.155 mol) in 150 ml pyridine as dispersing medium. The reaction medium is agitated overnight. The modified wool is removed and washed with ice-water. The washed modified wool is then placed in a solution of 13.62 g (0.052 mol) of P-hexyl-P,P-diphenylphosphine in 100 ml of acetonitrile and the reaction mixture is agitated overnight. The modified wool is then removed from the reaction medium, washed sequentially with acetonitrile, brine and water and dried in air.

Example 8

Preparation of
1-hexyl-1-thionium-4-thiacyclohexane bromide

The sulfonium salt 1-hexyl-1-thionium-4-thiacyclohexane bromide is prepared by adding 63.3 g (0.201 mol) of 1-bromohexadecane in 150 ml of ethyl acetate to 25 g (0.201 mol) of 1,4-dithiane in 250 ml of ethyl acetate. The solution mixture is stirred. The resultant precipitate is collected by suction filtration and washed with ether and dried under vacuum.

Example 9

Preparation of Antiviral Cotton Cloth with
1-hexyl-1-thionium-4-thiacyclohexane bromide A 25 g sample of 100% cotton cloth is placed in a solution of 29.5 g of the activating agent p-toluenesulfonyl chloride (0.155 mol) in 150 ml pyridine as dispersing medium. The reaction medium is agitated overnight. The modified cotton cloth is removed and washed with ice-water. The washed modified cotton cloth is then placed in acetonitrile with 1-hexyl-1-thionium-4-thiacyclohexane bromide (62.4 g, 0.155 mol) and is agitated overnight. The modified cotton cloth is then removed from the reaction mixture, washed sequentially with acetonitrile, brine and water, and dried in air.

Example 10

Application of modified DABCO detergent to
polyester fabric

The agent, bis-1',3'-(1-hexyl)-1,4-diazoniabicyclo[2.2.2]octane-2'-propanol tetrachloride, is placed in an aqueous solution (10% of agent by weight) and the polyester to be treated is saturated with this solution. The polyester fabric is pressed under a roller to remove excess liquid and then heated at 400° F. for 30 sec. to cause dissolution in the polyester material, and then cooled to ambient temperature.

Example 11

Preparation of DABCO in PVC

To a preparation of PVC prepared for finishing and heated to 350° F. is added the agent bis-1',3'-(1-hexyl)-1,4-diazoniabicyclo[2.2.2]octane-2'-propanol tetrachloride in an amount of 10 g/square meter of finished surface. After pressing and cooling samples the surface is antiviral.

We claim:

1. A method for protecting a surface from viral contamination, the method comprising converting the surface to an antiviral surface having the formula (I):

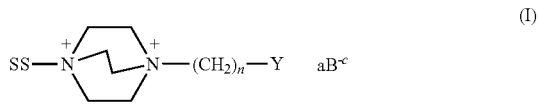

(I)

wherein:

SS represents a solid, macro surface comprising polymeric molecules having more than one primary hydroxyl group;

n represents an integer from 2-8;

Y represents $-NR_2$, $-^+NR_3$, $-PR_2$, $-^+PR_3$, $-OH$, $-SH$, $-SR$, $-^+SR_2$, $-SO_3^-$, $-SO_2-OR$, $-OR$, $-C(O)R$, $-C(O)OR$, or a diazabicyclo[2.2.2]octane derivative selected from:

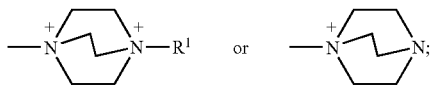 or 

R independently represents H, $C_{1-4}$ alkyl, or phenyl;
$R^1$ represents H, $C_{1-4}$ alkyl, phenyl, $-NR_2$, $-PR_2$, $-{}^+PR_3$, $-OH$, $-SH$, $-SR$, $-{}^+SR_2$, $-SO_3^-$, $-OR$, $-C(O)R$, $-C(O)OR$, or $-SO_2-OR$;
B represents an anion;
a represents an integer;
c represents the valence of B, and is equal to 1-3;
wherein a×c represents a number such that the compound is charge balanced; and
with the proviso that the macro surface is not α-cyclodextrin or β-cyclodextrin.

2. A method for protecting a polymeric material from viral contamination, the method comprising converting the polymeric material to a solid antiviral composition comprising
a) a polymeric material that is solid at room temperature and molten at elevated temperatures and, embedded therein;
b) a compound of formula (II):

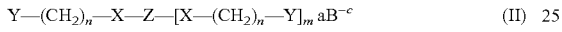 (II)

wherein:
Z represents a modified polyol having more than one primary hydroxyl group in the unmodified state, wherein at least two of the primary hydroxyl groups have been replaced by $X-(CH_2)_n-Y$ groups;
X represents

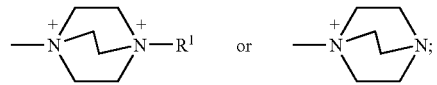

n independently represents an integer from 2-8;
Y represents $-NR_2$, $-{}^+NR_3$, $-PR_2$, $-{}^+PR_3$, $-OH$, $-SH$, $-SR$, $-{}^+SR_2$, $-SO_3^-$, $-SO_2-OR$, $-OR$, $-C(O)R$, $-C(O)OR$, or a diazabicyclo [2.2.2] octane derivative selected from:

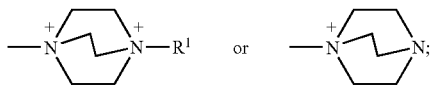 or 

R independently represents H, $C_{1-4}$ alkyl, or phenyl;
$R^1$ represents H, $C_{1-4}$ alkyl, phenyl, $-NR_2$, $-PR_2$, $-{}^+PR_3$, $-OH$, $-SH$, $-SR$, $-{}^+SR_2$, $-SO_3^-$, $-OR$, $-C(O)R$, $-C(O)OR$, or $-SO_2-OR$;
m represents any number up to $m^1-1$ wherein $m^1$ represents the number of primary hydroxyl groups in the polyol in the unmodified state;
B represents an anion;
a represents an integer; and
c represents the valence of B, and is equal to 1-3;
wherein a×c represents a number such that the compound is charge balanced.

* * * * *